US008865233B2

(12) United States Patent
Gao et al.

(10) Patent No.: US 8,865,233 B2
(45) Date of Patent: *Oct. 21, 2014

(54) COMPOSITIONS AND METHODS FOR TREATING *DEMODEX* INFESTATIONS

(71) Applicant: TissueTech, Inc., Doral, FL (US)

(72) Inventors: Ying-Ying Gao, Quanzhou (CN); Scheffer Tseng, Pinecrest, FL (US)

(73) Assignee: Tissuetech, Inc., Doral, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,283

(22) Filed: Apr. 8, 2013

(65) Prior Publication Data

US 2013/0224272 A1 Aug. 29, 2013

Related U.S. Application Data

(60) Continuation of application No. 12/771,705, filed on Apr. 30, 2010, now Pat. No. 8,455,015, which is a division of application No. 11/846,961, filed on Aug. 29, 2007, now Pat. No. 8,128,968.

(51) Int. Cl.
*A61K 36/61* (2006.01)
*A61K 31/045* (2006.01)
*A61K 9/00* (2006.01)
*A61K 31/35* (2006.01)

(52) U.S. Cl.
CPC ............... *A61K 31/045* (2013.01); *A61K 36/61* (2013.01); *A61K 9/00* (2013.01); *A61K 31/35* (2013.01)
USPC .......................................... 424/725; 514/725

(58) Field of Classification Search
USPC .......................................... 424/725; 514/724
IPC ........................................................ A61K 36/61
See application file for complete search history.

(56) References Cited

U.S. PATENT DOCUMENTS

| 4,215,113 | A | 7/1980 | Eriksson et al. |
| 4,745,100 | A | 5/1988 | Gilbard et al. |
| 4,900,753 | A | 2/1990 | Sutherland et al. |
| 5,033,252 | A | 7/1991 | Carter et al. |
| 5,052,558 | A | 10/1991 | Carter et al. |
| 5,208,257 | A | 5/1993 | Kabara |
| 5,323,907 | A | 6/1994 | Kalvelage |
| 5,444,043 | A | 8/1995 | Fenical et al. |
| 5,888,984 | A | 3/1999 | Brown |
| 6,022,529 | A | 2/2000 | Rock et al. |
| 6,197,305 | B1 | 3/2001 | Friedman et al. |
| 6,541,042 | B1 | 4/2003 | Frater-Schroder et al. |
| 6,649,660 | B2 | 11/2003 | Ninkov |
| 7,121,666 | B2 | 10/2006 | Tseng et al. |
| 8,128,968 | B2 | 3/2012 | Gao |
| 8,440,240 | B2 | 5/2013 | Gao et al. |
| 2001/0051184 | A1 | 12/2001 | Heng |
| 2003/0040504 | A1 | 2/2003 | Gans et al. |
| 2004/0197364 | A1 | 10/2004 | Brown |
| 2004/0235742 | A1 | 11/2004 | Mita et al. |
| 2004/0254165 | A1 | 12/2004 | Soumyanath et al. |
| 2005/0008714 | A1 | 1/2005 | Enan |
| 2005/0084545 | A1 | 4/2005 | Pipko et al. |
| 2005/0220742 | A1* | 10/2005 | Breen .......................... 424/70.1 |
| 2006/0068044 | A1 | 3/2006 | Reynolds |
| 2006/0147408 | A1 | 7/2006 | Reitz |
| 2006/0188492 | A1 | 8/2006 | Richardson et al. |
| 2007/0003590 | A1 | 1/2007 | Warburton |
| 2007/0020304 | A1 | 1/2007 | Tamarkin et al. |
| 2009/0061025 | A1 | 3/2009 | Gao |
| 2009/0137533 | A1* | 5/2009 | Adkins, Jr. .................... 514/152 |
| 2010/0011989 | A1 | 1/2010 | Arita et al. |
| 2010/0273870 | A1 | 10/2010 | Gao et al. |
| 2012/0004320 | A1 | 1/2012 | Gao et al. |

FOREIGN PATENT DOCUMENTS

| AU | 559001 A | 2/1987 |
| DE | 19824681 A1 | 12/1999 |
| EP | 734727 | 10/1996 |
| GB | 2362574 | 11/2001 |
| JP | 04198131 | 7/1992 |
| WO | WO-01-12225 | 2/2001 |
| WO | WO-2006-089348 | 8/2006 |
| WO | WO-2006-119174 A1 | 11/2006 |
| WO | WO-2009-032773 | 3/2009 |

OTHER PUBLICATIONS

"Isoprophyl alcohol" website, (http://web.archive.org/web/20060430103325/http://www.osha.gov/SLTC/healthguidelines/isopropylalcoholo/recognition.html—internet archived version from Apr. 30, 2011.
"Safety data for terpinen-4-ol" [online][retrieved on Nov. 30, 2011] Retrieved from the Internet:_http://msds.chem.ox.ac.uk/TE/terpinen-4-ol.html.
Balaban and Bobick, "Integumentary System," The Handy Anatomy Answer Book, 2008, p. 41 and 46, Visible Ink Press, Canton, MI.
Barreiro-Iglesias et al, "Incorporation of small quantities of surfactants as a way to improve the rheological and diffusional behavior of carbopol gels", J. Controlled Release, 77:59-75 (2001).
Biju et al., "Tea tree oil concentration in follicular casts after topical delivery: determination by high-performance thin layer chromatography using a perfused bovine udder model," J. Pharmaceutical Sciences 94: 240-245 (2005).
Brenan, J.A. et al., "Evaluation of patch testing in patients with chronic vulvar symptoms," Australas. J. Dermatol. 37:40-43 (1996).
Brophy, J .J., "Gas Chromatographic Quality Control for Oil of *Melaleuca* Terpinen4-ol Type (Australian Tea Tree)," J. Agric. Food Chem. 37:1330-1335 (1989).

(Continued)

Primary Examiner — Chris R Tate
(74) Attorney, Agent, or Firm — Wilson Sonsini Goodrich & Rosati

(57) ABSTRACT

Compositions containing about 0.6% to about 20% of tea tree oil are described. Some compositions are in the form of solutions, suspensions, spray, lotions, gels, pastes, medicated sticks, balms, cleansers (including shampoos and soaps), creams, or ointments. Also described are compositions and methods for use in treating ocular *Demodex* infestations and related conditions using such compositions.

16 Claims, 2 Drawing Sheets

(56) References Cited

OTHER PUBLICATIONS

Caelli et al., "Tea tree oil as an alternative topical decolonization agent for methicillin-resistant *Staphylococcus aureus*," J. Hospital Infection 46:236-237 (2000).
Carbopol Polymers for Pharmaceutical Delivery Applications, Drug Delivery, [from the internet: http.//drugdeliverytech.com/ME2/dirmod.asp?] Sep. 2003, vol. 3, No. 6 [retrieved from the internet May 14, 2012].
Cork et al., "New perspectives on epidermal barrier dysfunction in atopic dermatitis: Gene-environment interactions," J. Allergy Clin Immunol, Jul. 2006, 118(1):3-21.
Downs, A.M. et al., "Monoterpenoids and tetralin as pediculocides," Acta Dermatovenereologica 80(1):69-70 (2000).
Draelos et al., "Prevention of Cosmetic Problems," Preventive Dermatology, 2010, R. A. Norman (ed.), pp. 173-186, Springer-Verlag London Limited.
Dryden et al., "A randomized, controlled trial of tea tree topical preparations versus a standard topical regimen for the clearance of MRSA colonization," J. Hospital Infections 56: 283-286 (2004).
Dutton et al., "Anatomy of the Eyelids," Diagnostic Atlas of Common Eyelid Diseases, 2007, pp. 1-10.
Edsman et al, "Rheological evaluation and ocular contact time of some carbomer gels for ophthalmic use," Int. J. Pharm. 137(2):233-241 (1996).
English, F.P. and Nutting, W.B., "Demodicosis of ophthalmic concern," Am. J. Ophthalmol. 91:362-372 (1981).
EP 08798898.6 Search Report mailed Feb. 1, 2011.
Ford, R.A. et al., "Monographs on fragrance raw materials," Food Chem. Toxicol. 26:407 (1988).
Fulk GW, et al., "Pilocarpine gel for the treatment of demodicosis—a case series," Optom. Vis. Sci. 73:742-5 (1996).
Gao et al., "Clinical treatment of ocular demodecosis by lid scrub with tea tree oil," Cornea 26(2):136-143 (2007).
Gao et al., "High prevalence of ocular *Demodex* in lashes with cylindrical dandruffs and in vitro and in vivo killing studies," Inv. Ophthalmology Vis Science 46(Suppl):2655 (2005).
Gao, Y.Y. et al., "In Vitro and In Vivo killing of ocular *Demodex* by tea tree oil," Br. J. Ophthalmol. 89:1468-1473 (2005).
Gao, Y.Y. et al., "High Prevcalence of *Demodex* in Eyelashes with Cylindrical Dandruff," IOVS 46(9):3089-3094 (2005).
Gibney et al, "Skin and subcutaneous adipose layer thickness in aduts with diabetes at sited used for insulin injections: implications for needle length recommendations," Current Medical Research & Opinion, 2010, 26(6):1519-1530.
Jewett and Baker, "Skin and Composite Grafts," Principles of Nasal Reconstruction, 2011, S. R. Baker (ed), pp. 133-161, Sprinter Science + Business Media, LLC.
Journal of a society for the study of veterinary oriental medicine, No. 7 p. 20-23 (2001).
Junk AK et al., "Topical Administration of metronidazole gel as an effective therapy alternative in chronic *Demodex* blepharitis—a case report," Klin. Monatsbl. Augenheilkd. 213:48-50 (1998).
Kheirkhah et al., "Corneal Manifestations of Ocular *Demodex* Infestation," J Ophthalmology 143(5):743-749 (2007).
Kheirkhah, A. et al., "Fluorescin Dye Improves Microscopic Evaluation and Counting of *Demodex* in Blepharitis With Cylindrical Dandruff," Cornea 26(6):697-700 (2007).
Lichtenstein et al., "Insecticidal and Synergistic Components Isolated from Dill Plants," J.Agr. Food Chem (1974), vol. 22, No. 4, pp. 658-664.
Martin et al., "Herbal medicines for treatment of bacterial infections: a review of controlled clinical trials," J. Antimicrobial Chemotherapy 51:241-246 (2003).
Material Safety Data. Sheet for (-)-Terpinen-4-ol, 97%, MSDS Creation Date: Jul. 16, 1996, Revision #2 Date: Jun. 5, 2001; [online][retrieved on Nov. 30, 2011] Retrieved from the Internet: http://129.132.235.48/cheminfo/servlet/org.dbcreator.MainServlet?sort=&query=msds.msdsID%D20223&target=msds&action=PowerSearch&from=0&history=off&sort%3D%3E~entry.int Value=&realQuery=entry._structureID%3D4641903&format=ccd &searchTemplate=rn.value%3D%3D%3F&searchValue=20126-76-5&options=brandqtyoffer.
Material Safety Data Sheet for 4-Carvomenthertol. 92+%, FCC; Date Printed: Jan. 13, 2008, Date Updates: Feb. 4, 2006, Version 1.1;; [online][retrieved on Nov. 30, 2011] Retrieved from the Internet: http://www.msdsonline.com/.
Material Safety Data Sheet for Terpinen-4-ol, 97% ACC#04227; Fisher Scientific UK Web Catalogue; MSDS Creation Date: Jan. 16, 2002, Revision #1 Date: Oct. 5, 2004; ; [online][retrieved on Nov. 30, 2011] Retrieved from the Internet: http://www.msdsonline.com/.
Material Safety Data Sheet for Tetpinen-4-ol, 97% ACC# 04227; MSDS Creation Date: Jan. 16, 2002, Revision #1 Date: Oct. 5, 2004; ; [online][retrieved on Nov. 30, 2011] Retrieved from the Internet: http://www.msdsonline.com/.
Material Safety Data Sheet for Terpinen-4-ol, 97% ACC# 04227; MSDS Creation Date: Jan. 16, 2002; ; [online][retrieved on Nov. 30, 2011] Retrieved from the Internet: http://www.msdsonline.com/.
Mills, C. et al., "Inhibition of acetylcholinesterase by Tea Tree oil," J. Pharm. Pharmacol. 56:375-379 (2004).
Mohamed, et al. "Effect of some ophthalmic vehicles on in-vivo performance of xylocaine hydrochloride in rabbits eye," Pharm Ind., 52(12):1556-1558 (1990).
Mondello, F. et al., "In vivo activity of terpenin-4-ol, the main bioactive component of *Melaleuca alternifolia* Cheel (tea tree) oil against azole-susceptible and -resistant human pathogenic *Candida* species," BMC Infectious Diseases 6:158 (2006).
Norn, M.S., "*Demodex folliculorum*. Incidence and possible pathogenic role in the human eyelid," Acta Ophthalmol. Suppl. 108:7-85 (1970).
PCT/US08/74674 Search Report dated Feb. 17, 2009.
Priestley, C.M. et al., "Lethality of essential oil constituents towards the human louse, *Pediculus humanus*, and its eggs," Fitotherapia 77(4):303-309 (2006).
Reichling et al., "In vitro studies on release and human skin permeation of Australian tea tree oil (TTO) from topical formulations," Eur. J. Pharmaceutics Biopharma. 64:222-228 (2006).
Richards, Ira, Ph.D., "Skin," Principles and Practice of Toxicology in Public Heath, 2008, pp. 203-211, Jones and Bartlett Publishers, Inc., Boston, MA.
Simpson, E.L. et al., "Prevalence of botanical extract allergy in patients with contact dermatitis," Dermatitis 15:67-72 (2004).
Traina et al., "In vitro acaricidal activity of four monoterpenes and solvents against *Otodectes cynotis* (Acari: Psoroptidae)," Exp. Appl. Acarology 37:141-146 (2005).
U.S. Appl. No. 11/911,956 Final Office Action mailed Jul. 30, 2010.
U.S. Appl. No. 11/911,956 Final Office Action mailed Sep. 9, 2011.
U.S. Appl. No. 11/911,956 Non-Final Office Action mailed Apr. 16, 2010.
U.S. Appl. No. 11/911,956 Non-Final Office Action mailed Mar. 23, 2011.
U.S. Appl. No. 13/181,767 Non-Final Office Action mailed Aug. 3, 2012.
U.S. Appl. No. 11/846,961 Advisory Action mailed Mar. 25, 2009.
U.S. Appl. No. 11/846,961 Final Office Action mailed Jan. 14, 2009.
U.S. Appl. No. 11/846,961 Final Office Action mailed Jun. 30, 2010.
U.S. Appl. No. 11/846,961 Office Action mailed Dec. 30, 2009.
U.S. Appl. No. 11/846,961 Office Action mailed Jul. 28, 2008.
U.S. Appl. No. 12/771,705 Non-Final Office Action mailed Aug. 3, 2012.
Walton et al., "Acaricidal Activity of *Melaleuca alternifolia* (Tea Tree) oil," Arch. Dermatol. 140:563-566 (2004).
Website document entitled Ord River Tea Tree Cream 10% Oil- 50g', downloaded Jan. 25, 2011 from website http://www.academyhealth.com/ordriteatcr.html, 2 pages.
U.S. Appl. No. 11/846,961 Non-Final Office Action dated Apr. 8, 2011.
U.S. Appl. No. 12/771,705 Advisory Action dated Jan. 26, 2012.
U.S. Appl. No. 12/771,705 Non-Final Office Action dated Mar. 4, 2011.
U.S. Appl. No. 12/771,705 Non-Final Office Action dated Oct. 12, 2011.
U.S. Appl. No. 13/856,638 Non-Final Office Action dated Feb. 5, 2014.

* cited by examiner

COMPOSITIONS AND METHODS FOR TREATING *DEMODEX* INFESTATIONS

CROSS-REFERENCE

This application is a continuation application of U.S. patent application Ser. No. 12/771,705 filed on Apr. 30, 2010, which is a division of U.S. patent application Ser. No. 11/846,961 filed on Aug. 29, 2007, now issued as U.S. Pat. No. 8,128,968 on Mar. 6, 2012, all of which are incorporated herein by reference in their entirety.

BACKGROUND OF THE INVENTION

*Demodex* mites (of the class Arachnid and order Acarina) are microscopic ectoparasites that commonly infest the pilosebaceous unit of the skin. Among a wide range of reported species, at least *Demodex folliculorum* (*D. folliculorum*) and *Demodex brevis* (*D. brevis*) are found on the human body surface. Both *Demodex* species often coexist and preferentially gather at the same skin area of the face, cheeks, forehead, nose, and external ear tract, where active sebum excretion favors their habitat and breeding. Adult *Demodex* mites eventually die after a life cycle of 14 to 18 days, and their expansion is dependent on successful copulation by adult mites. Copulation takes place in the opening of the hair follicle (near the skin surface). Afterwards, the gravid female moves to the sebaceous gland to deposit eggs, which give rise to larvae and then protonymphs. A protonymph is brought to the opening of the hair follicle and gives rise to a deutonymph, which crawls onto the skin surface and re-enters a hair follicle to become an adult. Therefore, during a life cycle, if adult *Demodex* can successfully copulate and produce the next generation, the extent of infestation will increase in the host.

*Demodex* infestation is non-existent in healthy children, increases in an age-dependent manner, and is found probably 100% in elderly skin, unless eradicating measures are taken. The prevalence of *Demodex* infestation is higher in unhealthy skin than in normal skin. Overgrowth of these mites is linked to blepharitis (an inflammation of the eyelids), and other inflammation-associated conjunctival and corneal abnormalities. Blepharitis occurs as an ulcerous (staph) or nonulcerous (seborrheic) form, or a combination of both. Patients who suffer from blepharitis as a result of an ocular *Demodex* infestation often present a number of symptoms such as foring body sensation, redness and itching. Uncontrolled ocular *Demodex* infestation in eyelids may cause mal-directed lashes (trichiasis), meibomian gland dysfunction leading to lipid tear deficient dry eye, conjunctival inflammation (conjunctivitis), and sight-threatening corneal abnormalities. The symptoms can become severe enough that the patient may require surgery to achieve relief.

Rosacea is a chronic dermatological disease that affects the skin, usually the face, and sometimes the eyes. Inflammatory rosacea causes persistent redness and pink bumps referred to as papules, and pustules on the skin. Eye inflammation also may occur, with symptoms often including sensitivity to light, blurred or otherwise impaired vision, redness, dryness, itching, burning, tearing, and the sensation of having grit or sand in the eye. Inflammation of the eye is more apparent in advanced stages of rosacea, where the skin thickens and becomes a deep shade of red. Current treatments include oral antibiotics, e.g., tetracycline or doxycycline. If infections of the eyelids develop, physicians may recommend scrubbing the eyelids with diluted baby shampoo. Steroid eye drops may be prescribed in the case of severe infection.

Acne, including acne vulgaris and acne rosacea, is yet another chronic dermatological condition that is difficult to treat. Over-the-counter products for treatment of acne, including benzoyl peroxide and aluminium chlorhydroxide/sulphur can help reduce, but not cure, acne. Prescription treatments, including antibiotics, retinoids, and certain hormone pills, can improve acne, but can have serious adverse effects.

*Demodex* can also infest mammalian quadrupeds, in particular domestic animals, especially dogs, causing demodetic mange. The *Demodex* mite burrows into hair follicles and sebaceous glands of the animal, often causing severe dermatitis, infection, and discomfort. Demodetic mange, particularly in dogs, presents a difficult clinical problem for veterinarians, as it can involve the face and the entire body of the animal in some cases. Existing treatments can be expensive and are not always effective, with the result that affected animals are sometimes euthanized. Mange can also be caused by the burrowing parasitic mite *Sarcoptes*, which causes scabies, and *Chorioptes*. The *Cheyletiella* mite causes a condition known as "walking dandruff." In cats, notoedric mange is a burrowing mite infestation that is difficult to treat.

SUMMARY OF THE INVENTION

Compositions are described herein containing about 0.6% to about 20% of tea tree oil. In some embodiments, such compositions are in the form of solutions, suspensions, spray, lotions, gels, pastes, medicated sticks, balms, cleansers (including shampoos and soaps), creams, or ointments. In some embodiments, the compositions are in the form of an ointment. Also described herein are compositions and methods for use in treating ocular *Demodex* infestations and related conditions.

In one aspect are dermatologic or ophthalmic compositions comprising about 0.6% to about 20% w/w tea tree oil, about 3.0% to about 15% w/w tea tree oil, about 4% to about 10% w/w tea tree oil, or about 5% tea tree oil, and a dermatologically and/or ophthalmically acceptable base. In some embodiments, the dermatologically and/or ophthalmically acceptable base is an ointment base. In some embodiments, the composition is indicated for the treatment of a *Demodex* infestation.

In another aspect are dermatologic or ophthalmic compositions for relief of ocular itching, redness of the eye, soreness of the eye, ocular inflammation, or blurred vision, wherein the compositions comprise about 0.6% to about 20% w/w tea tree oil, about 3.0% to about 15% w/w tea tree oil, about 4% to about 10% w/w tea tree oil, or about 5% tea tree oil, and a dermatologically and/or ophthalmically acceptable base.

In another aspect are dermatologic or ophthalmic compositions for treating a *Demodex* infestation (or for relief of symptoms associated with such conditions), where the dermatologic or ophthalmic compositions comprise about 1% to about 20% terpinen-4-ol, about 0.3% to about 5.6% γ-terpinene, about 0.2% to about 3% 1,8 cineole, or about 0.2% to about 2.6% α-terpinene, or any combination thereof, and a dermatologically and/or ophthalmically acceptable base (e.g., an ointment base).

In another aspect are dermatologic or ophthalmic compositions for relief of ocular itching, redness of the eye, soreness of the eye, ocular inflammation, or blurred vision, where the dermatologic or ophthalmic compositions comprise about 1% to about 20% terpinen-4-ol, about 0.3% to about 5.6% γ-terpinene, about 0.2% to about 3% 1,8 cineole, or about 0.2% to about 2.6% α-terpinene, or any combination thereof, and a dermatologically and/or ophthalmically acceptable base (e.g., an ointment base).

In another aspect are methods for treating ocular *Demodex* infestation or *Demodex*-induced blepharitis (or for relief of symptoms associated with such conditions), where the methods include applying an ophthalmic composition comprising about 0.2% to about 20% w/w tea tree oil and an ophthalmically acceptable base (e.g., an ointment base) to the eyelid area of a subject in need thereof; massaging the composition onto the eyelid margin and eyelash root areas; and repeating the applying and massaging steps. In some embodiments, the subject being treated shows improvement in ocular itching, *Demodex* count, foreign body sensation, mal-directed lashes, lash falling, dry eye, redness, light-sensitivity, or any combination thereof. In some embodiments, the methods comprise applying an ophthalmic composition comprising about 5% w/w tea tree oil. In some embodiments, the subject to be treated is refractory to an anti-inflammatory, conventionally anti-microbial antibiotic, or an anti-allergy therapy for ocular *Demodex* infestation or *Demodex*-induced blepharitis. In some embodiments, the methods also include scrubbing the eyelid margin and eyelash with a tea tree oil solution or suspension before or after application of the above-described composition. In some embodiments, the tea tree oil solution is a tea tree oil shampoo.

In a further aspect are methods for treating ocular *Demodex* infestation or *Demodex*-induced blepharitis in a subject in need thereof, where the methods include applying an ophthalmic composition comprising about 1% to about 20% terpinen-4-ol, about 0.2% to about 5.6% γ-terpinene, about 0.2% to about 3% 1,8 cineole, or about 0.2% to about 2.6% α-terpinene, or any combination thereof, and an ophthalmically acceptable base (e.g., an ointment base) to the eyelid area; massaging the ophthalmic composition onto the eyelid margin and eyelash root areas; and repeating the applying and massaging steps until sufficient to migrate *Demodex* out of the lash follicle, to reduce *Demodex* copulation, to reduce *Demodex* presence, or to reduce *Demodex* re-infestations. In some embodiments, the subject to be treated is refractory to an anti-inflammatory, anti-microbial or an anti-allergy therapy for ocular *Demodex* infestation or *Demodex*-induced blepharitis. In some embodiments, the methods also include the eyelid margin and eyelash root areas with a tea tree oil solution or suspension, e.g., tea tree oil shampoo.

In a further aspect are articles of manufacture, where an article of manufacture includes a dispenser; an ointment comprising about 0.6% to about 20% w/w tea tree oil and a pharmaceutically acceptable ointment base; and instructions for use comprising the steps of applying the ointment to the affected area, massaging the ointment onto the affected area and repeating the applying and massaging steps until sufficient to migrate *Demodex* out of the affected area, to reduce *Demodex* count, or to reduce *Demodex* re-infestation. In some embodiments, the ointment comprises about 5% w/w tea tree oil.

In yet another aspect are methods for *Demodex*-induced rosacea, acne, and meibomian gland dysfunction in a subject in need, where the method includes applying a dermatologic or ophthalmic composition comprising about 0.6% to about 20% w/w tea tree oil and a dermatologically and/or ophthalmically acceptable base to the affected area; massaging the composition onto the affected area; and repeating the applying and massaging steps until sufficient to show an improvement in the disorder. In some embodiments, the dermatologically and/or ophthalmically acceptable base is an ointment base. In some embodiments, the methods also include scrubbing the affected area with a tea tree oil solution or suspension (e.g., tea tree oil shampoo).

In a further aspect are methods for treating *Demodex*-induced rosacea, acne, and meibomian gland dysfunction in a patient in need thereof, where the methods include applying a dermatologic or ophthalmic composition comprising about 1% to about 20% terpinen-4-ol, about 0.2% to about 5.6% γ-terpinene, about 0.2% to about 3% 1,8 cineole, or about 0.2% to about 2.6% α-terpinene, or any combination thereof, and a dermatologically and/or ophthalmically acceptable base to the eyelid area; massaging the composition onto the affected area; and repeating the applying and massaging steps until sufficient to show an improvement in the disorder. In some embodiments, the methods further include scrubbing the affected area with a tea tree oil solution or suspension (e.g., tea tree oil shampoo).

In another aspect are methods for treating sarcoptic mange, demodectic mange, chorioptic mange, notoedric mange, or a *cheyletiella* mite infestation on a mammal in need thereof, where the methods include applying an ointment comprising about 0.6% to about 20% w/w tea tree oil and a pharmaceutically acceptable ointment base to the affected area, and massaging the ointment onto the affected area.

In yet another aspect are methods for treating sarcoptic mange, demodectic mange, chorioptic mange, notoedric mange, or a *cheyletiella* mite infestation on a mammal in need thereof comprising: applying an ointment comprising about 0.6% to about 20% terpinen-4-ol, about 0.2% to about 5.6% γ-terpinene, about 0.2% to about 3% 1,8 cineole, or about 0.2% to about 2.6% α-terpinene, or any combination thereof, and a pharmaceutically acceptable ointment base to the affected area, and massaging the ointment onto the affected area.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
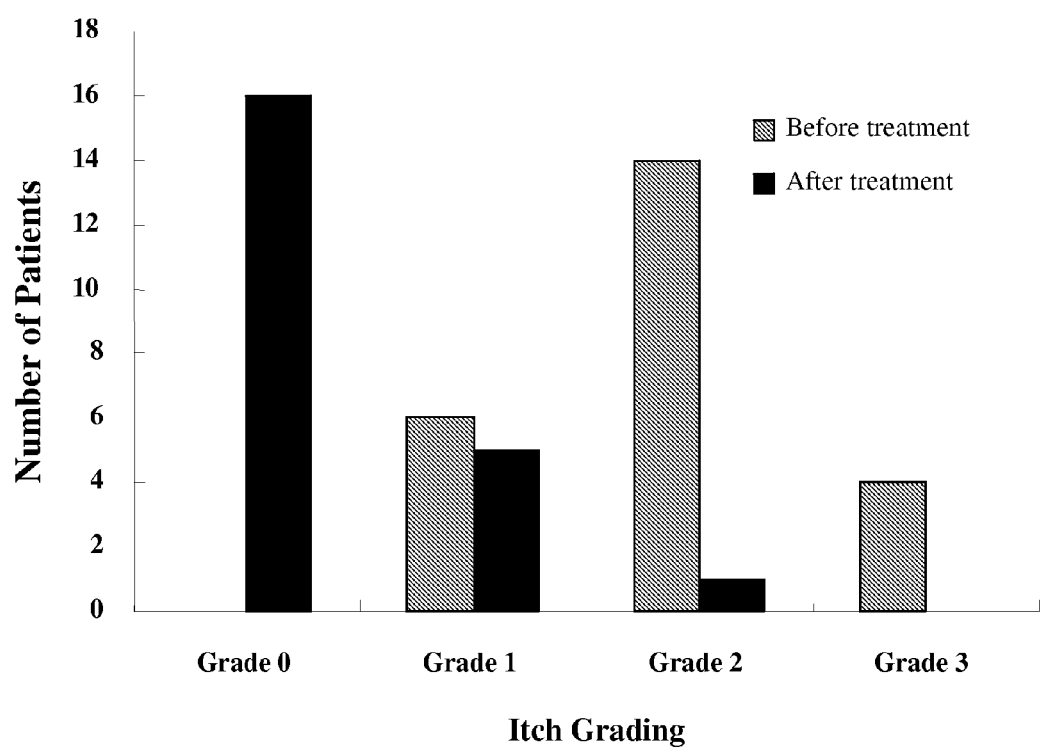
FIG. 1 is an illustrative bar graph showing ocular itch grading in demodecosis patients before and after treatment with an ointment containing 5% (w/w) tea tree oil ointment.

The appended claims particularly point out features set forth herein. A better understanding of the features and advantages of the present disclosure will be obtained by reference to the following detailed description that sets forth illustrative embodiments, in which the principles described herein are utilized.

Disclosed herein are demodicidal compositions and methods for their use in treating *Demodex* infestations (including ocular *Demodex* infestations), *Demodex*-induced blepharitis, rosacea, acne, meibomian gland dysfunction, mange, *cheyletiella* mite infestations, and related conditions.

*Demodex* infestations are commonly treated with systemic and topical administration of parasiticides. For example, ocular *Demodex* can be treated by performing a daily eyelid margin scrub with diluted shampoo alone or in combinations with a mercury oxide ointment, a metronidazole gel, or a pilocarpine gel applied to the base of the eye lashes. Unfortunately, these treatments frequently fail to eradicate this parasite, and therefore the infestation persists.

Accordingly, described herein is a new method for treating the aforementioned conditions. Without wishing to be bound by theory, it is believed that the compositions described herein promote migration of *Demodex* mites away from the treated area (e.g., the surface of an eyelid), inhibit reproduction of the mites, kill the mites, prevent re-infestation from the surrounding area, or provide a combination of any of the foregoing effects, which makes them useful for treating *Demodex* mite infestations and related conditions.

The compositions and methods described herein can be used to treat conditions that include, but are not limited to, *Demodex* infestation (e.g., ocular *Demodex* infestation), *Demodex*-induced blepharitis, rosacea, acne, meibomian gland dysfunction, chronic conjuctivitis, allergic conjunctivitis, trichiasis, sarcoptic mange, demodectic mange, chorioptic mange, notoedric mange, or a *Cheyletiella* mite infestation. Ocular *Demodex* infestations are accompanied by a number of symptoms including, e.g., itching, foreign body sensation, lash fallout, mal-directed lashes, redness, light sensitivity, or any combination of these symptoms.

*Demodex* species that can be controlled by the compositions described herein include, but are not limited to, *D. folicularum, D. brevis, D. canis, D. gatoi, D. bovis, D. equi, D. ovis, D. cati, D. phyloides*, and *D. caprae*. A subject to be treated with the compositions and methods described herein can be any mammal including, e.g., a human, a dog, a cat, a horse, a cow, a sheep, or a pig.

Compositions

The agents described herein may be administered topically and can be formulated into a variety of topically administrable compositions comprising an active ingredient and a dermatologically acceptable base and/or an ophthalmically acceptable base. Such compositions can be formulated, e.g., as solutions, suspensions, spray, lotions, gels, pastes, medicated sticks, balms, shampoos, creams or ointments. In one embodiment, the composition is the form of an ointment that can be applied in or around the eye of a mammal, including a human.

The active ingredients of such compositions can include tea tree oil and/or any combination of ingredients found in tea tree oil (see herein).

As used herein, "tea tree oil," i.e., 100% tea tree oil comprises the ranges of components listed in Table 1.

TABLE 1

Components of Tea Tree Oil (TTO)

| Ingredients | ISO 4730 Range (%) |
| --- | --- |
| 1. Terpinen-4-ol | >30 |
| 2. γ-Terpinene | 10-28 |
| 3. 1,8 Cineole | 0-15 |
| 4. α-Terpinene | 5-13 |
| 5. p-Cymene | 0.5-12 |
| 6. α-Terpineol | 1.5-8 |
| 7. δ-Cadinene | Trace-8 |
| 8. Aromadendrene | Trace-7 |
| 9. Ledene | 0.5-6.5 |
| 10. α-Pinene | 1-6 |
| 11. Terpinolene | 1.5-5 |
| 12. Limonene | 0.5-4 |

TABLE 1-continued

Components of Tea Tree Oil (TTO)

| Ingredients | ISO 4730 Range (%) |
| --- | --- |
| 13. Sabinene | Trace-3.5 |
| 14. Globulol | Trace-3 |
| 15. Viridiflorol | Trace-1.5 |

As used herein, a "dermatologically acceptable base," refers to one or more non-detergent excipients that do not cause irritation, inflammation, pain, or other harm to the skin when applied to the skin.

As used herein, an "ophthalmically acceptable base," refers to one or more non-detergent excipients that do not irritate or otherwise harm the surface of the eye when applied on the eyelid and eyelash area of the eye.

In some embodiments, a composition contains a dermatologically and/or ophthalmically acceptable base and about 0.2% to about 20% (w/w) tea tree oil, e.g., about 3% to about 15%, about 4% to about 10%, about 5%, or any other percent (w/w) of tea tree oil from about 0.2% to about 20%, e.g., 0.20%, 0.22% 0.30%, 0.40%, 0.50%, 0.60%, 0.80%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.7%, 5.2%, 5.7%, 6.2%, 6.7%, 7.2%, 7.7%, 8.2%, 8.7%, 9.2%, 9.5%, 10.0%, 10.5%, 11.2%, 11.5%, 12.0%, 12.4%, 12.9%, 13.3%, 13.5%, 13.7%, 14.0%, 14.5%, 15.0%, 15.5%, 16.0%, 16.6%, 17.0%, 17.4%, 18.0%, 18.5%, 18.8%, 19.0%, 19.2%, 19.4%, 19.5%, 19.6%, 19.7%, 19.8%, 19.9%, or 20% tea tree oil (w/w).

In some embodiments, a composition comprises a dermatologically and/or ophthalmically acceptable base and about 1% to about 20% (w/w) terpinen-4-ol, e.g., about 3% to about 15%, about 4% to about 10%, about 5%, or any other percent (w/w) of terpinen-4-ol falling between about 1% to about 20%, e.g., 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.5%, 5.2%, 5.7%, 6.2%, 6.7%, 7.4%, 7.7%, 8.2%, 8.5%, 9.2%, 9.5%, 10.0%, 10.5%, 11.2%, 11.5%, 12.0%, 12.4%, 12.9%, 13.3%, 13.5%, 13.7%, 14.0%, 14.7%, 15.0%, 15.5%, 16.0%, 16.6%, 17.0%, 17.4%, 18.3%, 18.5%, 18.8%, 19.0%, 19.2%, 19.4%, 19.5%, 19.6%, 19.7%, 19.8%, 19.9%, or 20% terpinen-4-ol.

In some embodiments, a composition comprises a dermatologically and/or ophthalmically acceptable base and about 0.2% to about 9% (w/w) γ-Terpinene, e.g., about 0.4% to about 5.2%, about 0.7% to about 5%, about 0.9% to about 4.4%, about 1.3% to about 4%, about 1.5% to about 3.6%, or any other percent (w/w) of terpinen 4-ol from about 0.2% to about 5.6%, or any other percent (w/w) of γ-Terpinene from about 1% to about 6%, e.g., 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.5%, 5.2%, 5.7% 6.2%, 6.7%, 7.4%, 7.7%, 8.2%, or 8.5% γ-Terpinene.

In some embodiments, a composition comprises a dermatologically and/or ophthalmically acceptable base and about 0.2% to about 10% (w/w) 1,8 cineole, e.g., about 0.4% to about 2.6%, about 0.6% to about 2.4%, 0.8% to about 2.2%, about 0.9% to about 2.0%, or any any other percent (w/w) of 1,8 cineole from about 0.2% to about 3%, e.g., 0.20%, 0.22% 0.30%, 0.40%, 0.50%, 0.60%, 0.80%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.7%, 5.2%, 5.7%, 6.2%, 6.7%, 7.2%, 7.7%, 8.2%, 8.7%, 9.2%, or 9.5% 1,8 cineole.

In some embodiments, a composition comprises a dermatologically and/or ophthalmically acceptable base and about 0.2% to about 4.5% (w/w) α-terpinene, e.g., about 0.3% to about 2.2%, about 0.5% to about 2.0%, about 0.6% to about 1.8%, or any other percent (w/w) of α-Terpinene from about 0.1% to about 4.5%, e.g., 0.20%, 0.22% 0.30%, 0.40%, 0.50%, 0.60%, 0.80%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2% α-terpinene.

In some embodiments, a composition comprises a pharmaceutically acceptable ointment and a combination two or more of about 0.2% to about 20% (w/w) terpinen 4-ol, 0.2% to about 5.6% (w/w) γ-Terpinene; about 0.2% to about 3% (w/w) 1,8 cineole; and about 0.3% to about 2.6% (w/w) α-terpinene.

In some embodiments, a dermatologically and/or ophthalmically acceptable base includes a pharmaceutically acceptable ointment base. Examples of suitable ointment bases include, but are not limited to oleaginous ointment bases such as petrolatum (e.g., liquid petrolatum or white petrolatum), plastibase, hard paraffin, white soft paraffin, yellow soft paraffin, liquid paraffin, emulsifying wax, microcrystalline wax, white bees wax, yellow bees wax, carnauba wax, wool wax (wool fat), mineral oil, olive oil, purified lanolin, anhydrous lanolin, and water soluble ointment bases such as polyethylene glycol (e.g., polyethylene glycol 400 or polyethylene glycol 3350), propylene glycol, polyoxyethylene, polyoxypropylene, or any combinations thereof.

In some embodiments, a dermatologically and/or ophthalmically acceptable base includes one or more polymers as suspending agents. Useful polymers include, but are not limited to, water-soluble polymers such as cellulosic polymers, e.g., hydroxypropyl methylcellulose, and water-insoluble polymers such as cross-linked carboxyl-containing polymers. A dermatologically and/or ophthalmically acceptable base can also include a dermatologically and/or ophthalmically acceptable mucoadhesive polymer, e.g., carboxymethylcellulose, carbomer (acrylic acid polymer), poly(methylmethacrylate), polyacrylamide, polycarbophil, acrylic acid/butyl acrylate copolymer, sodium alginate, or dextran.

In some embodiments, a dermatologically and/or ophthalmically acceptable base includes one or more viscosity enhancing agents. Examples of suitable viscosity enhancing agents include, but are not limited to, methyl cellulose, xanthan gum, gum tragacanth, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, acacia, corn starch, gelatin, or combinations thereof.

In some embodiments, a dermatologically and/or ophthalmically acceptable base includes one or more dermatologically and/or ophthalmically acceptable pH adjusting agents or buffering agents, including, but not limited to, acids such as acetic, boric, citric, lactic, phosphoric and hydrochloric acids; bases such as sodium hydroxide, sodium phosphate, sodium borate, sodium citrate, sodium acetate, sodium, lactate and tris-hydroxymethylaminomethane; and buffers such as citrate/dextrose, sodium bicarbonate and ammonium chloride. Such acids, bases and buffers are included in an amount required to maintain pH of the composition in a dermatologically and/or ophthalmically acceptable range.

In some embodiments, a dermatologically and/or ophthalmically acceptable base includes one or more dermatologically and/or ophthalmically acceptable salts in an amount required to bring osmolality of the composition into a dermatologically and/or ophthalmically acceptable range. Such salts include, but are not limited to, those having sodium, potassium or ammonium cations and chloride, citrate, ascorbate, borate, phosphate, bicarbonate, sulfate, thiosulfate or bisulfite anions; specific salts include, e.g., sodium chloride, potassium chloride, sodium thiosulfate, sodium bisulfite, and ammonium sulfate.

In some embodiments, a dermatologically and/or ophthalmically acceptable base includes one or more dermatologically and/or ophthalmically acceptable preservatives to inhibit microbial activity. Suitable preservatives include, but are not limited to, mercury-containing substances such as merfen and thiomersal; stabilized chlorine dioxide; and quaternary ammonium compounds such as benzalkonium chloride, cetyltrimethylammonium bromide and cetylpyridinium chloride.

In further embodiments, a dermatologically and/or ophthalmically acceptable base includes one or more dermatologically and/or ophthalmically acceptable surfactants to enhance physical stability, or for other purposes. Suitable nonionic surfactants include polyoxyethylerie fatty acid glycerides and vegetable oils, e.g., polyoxyethylene (60) hydrogenated castor oil; and polyoxyethylerie alkylethers and alkylphenyl ethers, e.g., octoxynol 10, octoxynol 40.

In yet other embodiments, a dermatologically and/or ophthalmically acceptable base includes one or more antioxidants to enhance chemical stability where required. Suitable antioxidants include, by way of example only, butylated hydroxytoluene (BHT), sodium ascorbate, ascorbic acid, sodium metabisulfite, and tocopherol. In certain embodiments, antioxidants enhance chemical stability where required.

Details on techniques for formulation may be found in the latest edition of *Remington's Pharmaceutical Sciences* (Maack Publishing Co., Easton, Pa.).

Methods for determining the presence and amounts of specific chemical components and byproducts thereof (e.g., degradation products) in any of the compositions described herein include, for example, an assay method can be based on the industry standard produced by the Australian Standard Method as 2782-1997, "Oil of Melaleuca, terpinen-4-ol type (Tree Tea Oil)" and following GLP set using Gas Chromatography (GC-FID) and Gas-chromatography mass spectrometry. See, e.g., Brophy et al. (1989), *J Agric Food Chem*, 37:1330-1335; and Mondello et al. (2006), *BMC Infect Dis*, 6:158.

Toxicity and therapeutic efficacy of such compositions can be determined by standard pharmaceutical procedures in cell cultures or experimental animals, for example, in accordance with the ISO 10993-1 standard for toxicology testing and in accordance with GLP (Good Laboratory Practice) regulations.

For example, cell culture assays can be used to assess the biocompatibility of a material through the use of isolated cells in vitro. These techniques are useful in evaluating the toxicity or irritancy potential of materials and chemicals and they provide an excellent way to screen material prior to in vivo tests. Specifically, the MEM elution assay can be performed on a series of dilutions of the compounds described herein. Each compond dilution is added to a monolayer of L-929 cells and then incubated. Afterwards, cells are examined microscopically for malformation, degeneration and lysis, and the test compound is scored for its cytopathic effect.

In another example, an ocular irritation test is designed to determine the ocular irritation and toxicity of solutions for up to 72 hours in rabbits' eyes. Generally, 3 rabbits with clinically normal eyes are used in a study. Rabbits' eyes are examined daily and scored using the Draize system. Before treatment and at 1, 24, 48 and 72 hours, the eyes of each rabbit are also examined with an ophthalmoscope and scored for ocular irritation using the McDonald-Shadduck method (slit-lamp and fluorescein stain).

Methods of Treatment

The compositions described herein can be used for the manufacture of a medicament for treating any of the foregoing conditions (e.g., an ocular *Demodex* infestation, rosacea, meibomian gland dysfunction, demodectic mange, etc.).

In some embodiments, where the condition to be treated is an ocular *Demodex* infestation, *Demodex*-induced blepharitis, or a related condition, the compositions described herein (e.g., a dermatogically or ophthalmically acceptable ointment) are administered (e.g., self administered) topically by gentle application to a subject's skin, or, if treating an ocular condition, the eyelid margin, skin, and eyelash roots, followed by massaging of the eyelid margin and skin from one end to the other, and repeating the applying and massaging steps until sufficient to migrate *Demodex* out of the lash follicle, to reduce *Demodex* copulation, to reduce *Demodex* presence, or to reduce *Demodex* re-infestation. In some embodiments, excess composition is left on the eyelid area is left on until the next treatment. In other embodiments, excess composition is wiped or washed away after massaging. In some embodiments, the eyelid margin, skin, and eyelash root areas are scrubbed with a tea tree oil solution or suspension prior to application of one of the ophthalmically acceptable compositions described herein. In other embodiments, the tea tree oil solution or suspension is used to scrub after one of the ophthalmically acceptable compositions described herein has been applied and massaged onto the eyelid margin, skin, eyelash root areas. The tea tree oil solution or suspension used for scrubbing can have any concentration of tea tree oil from about 2% to 100% tea tree oil, e.g., about 2%, 3%, 4%, 4.5%, 5%, 6%, 7%, 9.5%, 12%, 14.5% 17%, 19.5%, 22%, 24.5%, 27%, 29.5%, 32%, 34.5%, 37%, 39.5%, 42%, 44.5%, 47%, 49.5%, 52%, 54.5%, 57%, 60%, 62%, 64.5%, 67%, 69.5%, 72%, 74.5%, 77%, 79.5%, 82%, 84.5%, 87%, 89.5%, 92%, 94.5%, 97%, or 99.5% tea tree oil. In some embodiments, the tea tree oil solution is a tea tree oil shampoo, which is commercially available, e.g., Kato Sales, Inc. (Altamonte Springs, Fla., USA).

A number of endpoints can be used to evaluate the therapeutic efficacy of the methods described herein. For example, a reduction in one or more of ocular itching, *Demodex* count (i.e., *Demodex* presence), foreign body sensation, eyelash fallout, mal-directed lashes, dry eye, light sensitivity or eye redness are indicative of a successful treatment. Thus, in some embodiments, applying and massaging of an ointment to the eyelid is repeated until one or more of the just-described endpoints are attained.

In an exemplary embodiment, an ointment formulation is generated by mixing tea tree oil from Essential Oil Company, (Portland, Oreg., USA) with Vaseline to a final concentration (w/w) of 5% tea tree oil. Application and massage of 5% tea tree oil ointment is performed twice a day (e.g., once before noon and once before bedtime) for five minutes each, for a total treatment period of about four weeks.

The compositions containing the compound(s) described herein can be administered for prophylactic and/or therapeutic treatments. In therapeutic applications, the compositions are administered to a patient already suffering from an ocular *Demodex* infestation, *Demodex*-induced blepharitis, or a related condition, in an amount and duration of application time sufficient to cure or at least partially arrest the symptoms of the disease or condition. Amounts effective for this use will depend on the severity and course of the disease or condition, previous therapy, the patient's health status, weight, and response to the drugs, and/or the judgment of a treating physician.

In prophylactic applications, compositions containing the compounds described herein are administered to a patient susceptible to or otherwise at risk of an ocular *Demodex* infestation, *Demodex*-induced blepharitis, or a related condition.

In another embodiment, where the condition to be treated is rosacea, acne, meibomian gland dysfunction, or related disorder, the compositions described herein are ointment formulations administered (e.g., self administered) topically by gentle application to a subject's affected area (e.g., face, neck, or eyelid), followed by massaging of the affected area from one end to the other, and repeating the applying and massaging steps until sufficient to show an improvement in the disorder. In some embodiments, excess ointment left on the affected area is left on until the next treatment. In other embodiments, excess ointment is wiped away after massaging. In some embodiments, after excess ointment is wiped away, the affected area is scrubbed with any of the foregoing tea tree oil solutions or suspensions (e.g., a tea tree oil shampoo).

In another embodiment, where the condition to be treated is sarcoptic mange, demodectic mange, chorioptic mange, notoedric mange, or *cheyletiella* mite infestation on a mammal, the compositions described herein are ointment formulations administered topically to the mammal in need by gentle application to the mammal's affected area (e.g. head or entire body), followed by massaging of the affected area from one end to the other, and repeating the applying and massaging steps until sufficient to show an improvement in the disorder.

Once improvement of the patient's conditions has occurred based on an evaluation of one or more of the symptoms described herein, a maintenance dose of the composition is administered if necessary. Subsequently, the dosage or the frequency of administration, or both, can be reduced, as a function of the symptoms, to a level at which the improved condition is retained. Patients can, however, require intermittent treatment on a long-term basis upon any recurrence of symptoms.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation.

Combination Treatments

Compositions described herein can also be used in combination with other therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes.

In certain instances, it may be appropriate to administer at least one composition described herein in combination with another therapeutic agent. By way of example only, if one of the side effects experienced by a patient upon receiving one of the compounds described herein is skin irritation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used.

Therapeutically-effective dosages can vary when the drugs are used in treatment combinations, and methods such as (by way of example only) metronomic dosing, i.e., providing more frequent, lower doses in order to minimize toxic side effects, can be used to determine such doses. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more other agents, the compound provided herein may be administered either simultaneously with the agent(s), or sequentially.

In any case, the multiple therapeutic agents (one of which is a composition described herein) may be administered in any order or even simultaneously. If simultaneously, the multiple therapeutic agents may be provided in a single, unified form, or in multiple forms (by way of example only, either as a single ointment or as an ointment and a pill). One of the therapeutic agents may be given in multiple doses, or both may be given as multiple doses. If not simultaneous, the timing between the multiple doses may vary from more than fifteen minutes to less than four weeks. In addition, the combination methods, compositions and formulations are not to be limited to the use of only two agents; the use of multiple therapeutic combinations are also envisioned.

The dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents.

Exemplary Agents for Use in Combination Therapy: Agents for Treating Inflammation Where the subject is suffering from or at risk of suffering from a skin inflammation, an acaricidal composition can be used in with one or more of the following therapeutic agents in any combination: glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-$\alpha$ binding proteins (e.g., infliximab, etanercept, or adalimumab), abatacept, anakinra, interferon-$\beta$, interferon-$\gamma$, interleukin-2, allergy vaccines, antihistamines, antileukotrienes, beta-agonists, theophylline, or anticholinergics; antibiotics; tarcolimus, or retinoids.

Articles of Manufacture

For use in the applications described herein, kits and articles of manufacture are also described herein. The terms "kit" and "article of manufacture" are used as synonyms. Such kits can include a carrier, package, or container that is compartmentalized to receive one or more containers such as vials, tubes, and the like, each of the container(s) including one of the separate elements to be used in a method described herein. Preferably, containers (e.g., vials) containing a composition described herein are light-proof have a tight seal. For example, the container(s) can include one of the dermatologically or opthalmically acceptable compositions described herein, i.e., a dermatologically or opthalmically acceptable composition comprising 0.6 to 20% w/w tea tree oil. In an exemplary embodiment, the containers contain an ointment comprising about 5% w/w tea tree oil and a pharmaceutically acceptable ointment base, as disclosed herein. Suitable containers include, for example, bottles, vials, syringes, and test tubes. The containers can be formed from a variety of materials such as glass or plastic. Preferably, the container protects against certain wavelengths of light and prolonged high temperature, and/or the ingress of air. Preferably the container is a sealed, light-proof container.

The articles of manufacture provided herein contain packaging materials. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment. A wide array of topical formulations of the compounds and compositions provided herein are contemplated as are a variety of treatments for any of the diseases, disorders, or conditions associated with the acarinal species described herein.

Such kits optionally comprise a compound with an identifying description or label or instructions relating to its use in the methods described herein. For example, the kit may include instructions for use comprising the steps of applying the ointment to the affected area, massaging the ointment onto the affected area and repeating the applying and massaging steps until sufficient to migrate *Demodex* out of the affected area, to reduce *Demodex* count, or to reduce *Demodex* re-infestation.

A kit may include one or more additional containers, each with one or more of various materials desirable from a commercial and user standpoint for use of the compositions for treating *Demodex* described herein. Non-limiting examples of such materials include, but not limited to, buffers, diluents, carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Reference thereto evidences the availability and public dissemination of such information.

Example 1

5% Tea Tree Oil (TTO) Topical Formulation

TTO purchased from Essential Oil Company (Portland, Oreg., USA) was mixed with Vaseline (BaiHe Pharmacy, Quanzhou, China) to 5% (W/W) Tea Tree Oil Ointment (TTOO) in a sterile hood to obtain a 5% TTO topical formulation for treatment of, e.g., an ocular *Demodex* infestation.

Example 2

Treatment of Ocular Demedecosis with Daily Massage of a 5% Tea Tree Oil Ointment (TTOO)

The study was performed at the Second-affiliated Hospital of Fujian Medical University, China, with an approval from the Institutional Ethics Committee. A written informed consent was obtained from every patient. A total of 24 patients were enrolled with the complaints of eye itching and other symptoms and carried a diagnosis of either chronic conjunctivitis or allergic conjunctivitis despite prior treatments with topical antibiotics (Levofloxacin, Tobramycin, Ofloxacin), steroids (Dexamethasone, Prednisolone), and artificial tears. They were confirmed to have ocular *Demodex* based on a modified *Demodex* microscopy assay as described in, e.g., Gao et al. (2005), *Invest Opthal Vis Sci,* 46(9):3089-3094. During the first (baseline) examination, patient symptoms including itching were recorded as 0 (none), 1 (mild and occasional without disturbing daily activities), 2 (moderate and requiring the need of rubbing the eye or using eye drops), and 3 (severe, more constant, and disturbing daily activities even with the application of the eye drops). Symptoms were recorded before and 4 and 8 weeks after treatment.

Patients performed the following self-treatment procedure at home: after washing the face and lids with baby shampoo or soap and rinsing with warm water, a small amount of 5% tea tree oil ointment was smeared onto both middle fingers. With the eyes closed, both middle fingers applied a gentle pressure applied on the lid margin and lash roots while massaging the lid margin from one end to the other, which counted as one stroke. A total of 120 back and forth strokes for 5 minutes were applied, leaving in the end the residual 5% tea tree oil ointment without washing before the next treatment. The very first treatment was carried out in the office under doctor's instruction while the remaining treatments were performed at the home, twice a day before noon nap and at night before going to bed. Such a treatment was practiced for 4 weeks, during which time the patient was seen once a week, and 4 weeks later. In addition, the patient was also instructed to cease using facial cosmetics, and to wash the hair, the face, nostrils, the external ear and the neck with soap daily. No other topical medication was used during the tea tree oil ointment treatment.

The data were reported as means±SD and analyzed by MicroSoft Excel™ (MicroSoft, Redmont Wash.). The data between groups were evaluated by two-tailed t test, where $P<0.05$ was considered statistically significant.

Figure 2:
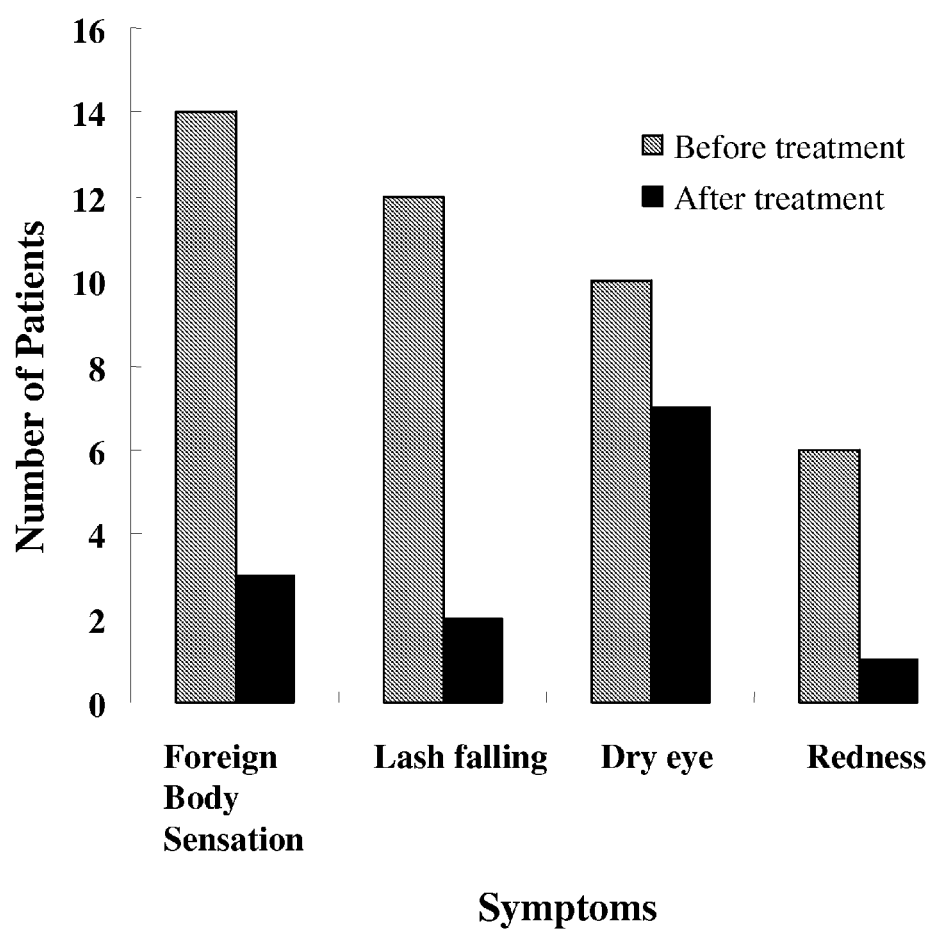
FIG. 2 is an illustrative bar graph showing the incidence of symptoms among demodecosis patients before and after treatment with an ointment containing 5% (w/w) tea tree oil ointment.

These 24 patients included 10 males and 14 females with a mean age of 37.2±15.6 years. Before treatment, they all complained of different degrees of itching graded as 1 (n=6), 2 (n=14), and 3 (n=4) for a period ranging from 2 weeks to 2 years (FIG. 1). Other complaints included foreign body sensation (n=14), lash falling (n=12), dry eye (n=10), and redness (n=6) (FIG. 2). They had also consulted with multiple ophthalmologists for the aforementioned ocular irritation, been diagnosed as chronic conjunctivitis (n=20) or allergic conjunctivitis (n=4), and treated with topical antibiotics (Levofloxacin, Tobramycin, Ofloxacin et.al), steroids (Dexamethasone, Prednisolone), any anti-allergy (histamine) medication, and/or artificial tears. Routine eye examination disclosed diffuse (n=4) and sporadic (n=11) cylindrical dandruff in their eyelashes. However, mild injection of blood vessels was noted in the bulbar conjunctiva of 6 patients, and in the lid margin of 4 patients, but not in the remaining majority. We detected *Demodex* mites in all patients: the *Demodex* counts per 8 removed lashes were 2.3±1.5, 2.8±2.1 and 3.1±2.1 for patients with Grade 1, 2 and 3 itchiness, respectively (each $P>0.05$ between groups).

After 4 weeks of treatment by daily home lid massage with 5% tea tree oil ointment, lashes became clean in all except for 4 patients, which still had sporadic CD at lashes. The *Demodex* count dropped to zero in 19 patients (79%), and to 0.3±0.2 in the remaining 5 patients, collectively resulting in a significant reduction of the *Demodex* count ($P=0.002$). At the end of 8 weeks, the *Demodex* count remained zero in 15 patients. The complaint of ocular itching was also dramatically relieved, resulting in Grade 0 (n=16), 1 (n=5), 2 (n=1), and 3

(n=0) (FIG. 1, P<0.001). Other complaints also showed different degrees of relief after treatment, e.g., foreign body sensation (n=3, P=0.002) and lash falling (n=2, P=0.003), but not that of dryness (n=7, P=0.82) and redness (n=1, P=0.1) (FIG. 2). Overall, all patients felt that there was a considerably less weight in lids after the tea tree oil ointment treatment and did not report any irritation caused by the treatment.

Based on these results, we concluded that daily, at home, lid massage with 5% tea tree oil ointment resulted in a dramatic relief of itching and reduction of *Demodex* counts within one life cycle without causing any side effects. Thus, daily 5% tea tree oil ointment lid massage was effective for treatment of ocular demedecosis.

Example 3

Acaricidal Activity of Individual Tea Tree Oil Components

Each of the following individual tea tree oil ingredients are tested for acaricidal activity at a range of concentrations serially diluted from 0.5% to 30% in an in vitro *Demodex* killing assay as described below: Terpinen-4-ol, γ-Terpinene, α-Terpinene, α-Terpineol, Limonene, Sabinene, Aromadendrene, Ledene, α-Pinene, Terpinolene, δ-Cadinene, Viridiflorol, and Globulol.

For each assay, 50% tea tree oil is used as a positive control for acaridal activity, and 100% mineral oil is used as the negative control. The *Demodex* killing efficiency is measured by the survival time in minutes, reported as mean±SD (n=at least 5 adult mites), and compared among these ingredients by two-tailed t test, where p<0.05 is considered statistically significant.

Eyelashes with cylindrical dandruff are removed and examined under magnification to determine the presence of *Demodex* as previously reported in Gao et al., *Invest Opthalmol Vis Sci* (2005) 46:3089-94. If the epilated lash is found to contain live *Demodex*, solutions containing different tea tree oil ingredients will be added. If the epilated lash contains cylindrical dandruff, one drop of fluorescein solution made by wetting a fluorescein strip (FUL-GLO, Akron, Inc., Buffalo Grove, Ill., USA) with one drop of 0.9% NaCl solution will be added to reveal any embedded mites, according to Kheirkhah et al., *Cornea* 26:697-700 (2007). Since *Demodex* is more susceptible to acaricidal agents at an earlier stage of life, only test adult *Demodex* are tested as a more robust index of acaricidal activity. The mites are considered to be adult if they have 4 pairs of well-developed legs and stumpy body. The movement of the body and legs is continuously observed for 150 minutes post-addition of one of the foregoing test compounds at a particular concentration. As described in methods by Gao et al, *Br J Ophthalmol* 89:1468-1473 (2005), the survival time (ST) is defined as from the time when the solution is added to the time when the movement ceases. ST values of 150 minutes or greater indicate a lack of acaricidal activity, as shown in Gao et al. (2005), *Br J Opthamol*, 89:1468-1473.

Example 4

Clinical Studies

All clinical studies follow the Tenets of Helsinki Declaration of Human Studies and are conducted after the protocol/consent form has been approved by the Institutional Review Board.

The clinical studies enroll patients of either gender, ages≥21, and ethnic minorities compatible with the community population. We exclude children because *Demodex* infestation is uncommon in children, i.e., under the age of 18 years old. Furthermore, there is a recent report of perpubertal gynecomastia (enlargement of the breast) developed in three children with ages ranging from 4 to 10 after using over-the-counter personal care products containing lavender oil (all three cases) and tea tree oil (one case). Because in vitro studies also reveal that both lavender oil and tea tree oil containing ingredients that exert estrogenic and anti-androgenic activities, hence potentially eliciting endocrine-disrupting effects, we would also like to exclude those female adults with malignancies (such as breast cancers) that could be worsened by exposure to such activities. Furthermore, patients that have a history of a known fragrance allergy are also excluded.

The inclusion criteria are the presence of cylindrical dandruff during the external examination and microscopic confirmation of ocular *Demodex*. Briefly, at the slit lamp examination, two lashes with cylindrical dandruff are removed by fine forceps from each lid, and separately placed on a glass slide. Thus a total of 8 lashes on 4 slides are epilated, and covered by a coverslip. All lashes are examined under the microscope, and lashes with cylindrical dandruff are added with a drop of saline containing 0.5% fluorescein to dissolve the cylindrical dandruff. Under the microscope, the stage and type of *Demodex* mites is recorded and the number of *Demodex* is counted and the total number of mites in 8 lashes is registered as the *Demodex* count for that patient at that time.

All patients that meet the inclusion and exclusion criteria are enrolled from the Ocular Surface Center (Miami, Fla.), where patients with complicated and difficult ocular surface diseases are seen. All enrolled patients do not use any topical or systemic anti-inflammatory and anti-microbial medications during the study.

Before study and treatment, all patients receive routine history taking including grading of symptoms based on the scale provided in Ocular Surface Disease Index (OSDI). OSDI screens irritating symptoms of light sensitivity, gritty sensation, pain or soreness, blurred vision and poor vision (Subtotal A), and whether these symptoms manifest upon the following four activities including reading, driving at night, using computer, or watching TV (Subtotal B) and in the following three external environment such as windy condition, low humidity and air conditioner (Subtotal C). For each of the above twelve items, a score of 4 is assigned if the occurrence is "all the time," a score of 3 if the occurrence is "most of the time," a score of 2 if the occurrence is "half of the time", a score of 1 if the occurrence is "some of the time," and a score of 0 if the occurrence is "none or not applicable." Therefore, the highest total score is 48, and the lowest is 0.

All patients also receive external examination and photography to determine the extent of cylindrical dandruff in the upper eyelid, defined as "diffuse" (i.e., cylindrical dandruff found in more than 10 lashes) or "sporadic" (less than 10 lashes), and the *Demodex* sampling and counting according to the modified method (above). Patients with initial high *Demodex* counts, defined herein as having 10 mites/8 lashes, are less apt to be eradicated than those with initial low *Demodex* counts, defined as having ≤10 mites/8 lashes. Therefore, patients are randomized to either Study Group or Control Group using pre-assigned blocks to stratify this important variable.

All enrolled patients are evaluated weekly for the first month, for grading of symptoms and external examination and photography. At the end of the first month, the *Demodex* count is repeated. The same treatment regimen and examination is repeated for the second month. At the end of the second month, a third *Demodex* count is taken, and treatment is discontinued for one more month, when the final evaluation and the final *Demodex* count are repeated at the end of the third month.

To perform the lid scrub, in the office, after a drop of 0.5% proparacaine, a cotton applicator wetted in 50% tea tree oil in mineral oil is used to scrub the lash roots from one end to the other, counted as one stroke. A total of 6 strokes are applied to each lid. A dry cotton applicator is then used to remove excess tea tree oil from the lid margin. After 5 minutes, the second lid scrub is performed in the same manner. After another 5 minutes, the third lid scrub is applied. Eye irritation, if any, is graded using OSDI for each eye, and the eye is rinsed with non-preserved saline. At home, the patient mixes 0.5 ml of tea tree shampoo with tap water in both middle fingers. With eyes closed, the lids are massaged back and forth with a medium pressure for 3 minutes. The skin is then rinsed with clean water and dried with a face towel. Such home lid scrub is practiced twice daily.

To perform the lid massage, after washing the face and lids with soap and rinsing with warm water, a small amount of 5% tea tree oil ointment is smeared onto both middle fingers. With eyes closed, both middle fingers apply a gentle pressure on the lid margin and lash roots and massage the lid margin from one end to the other, each counting as one stroke, for a total of 120 back and forth strokes for 5 minutes. The remaining ointment is either washed away with a face cloth or left in the end without washing before the next treatment. The very first treatment is carried out in the office under the doctor's instruction/supervision while the remaining treatments are performed at home twice a day.

All patients are also instructed to cease using facial cosmetics, and to wash the hair, the face, nostrils, the external ear and the neck with soap daily. Bedding and pillow cases are washed with hot water and dried in a heated dryer immediately after the first office scrub, and once a week thereafter.

The safety outcome, defined by the occurrence (rate) of eye irritation noted after each treatment will be compared between Study Group and Control Group using Fisher's exact ($X^2$) test, where $p<0.05$ is considered statistically significant. The initial efficacy outcome is measured by the extent of reduction of the symptoms measured by OSDI scores, and of the *Demodex* count; both are measured as means±SD. They are compared within the group by comparing the final value to the baseline value using two-tailed t test, where $p<0.05$ is considered statistically significant. The final efficacy outcome is measured as the percentage (rate) of total eradication, which is registered in that patient if the *Demodex* count reaches zero for two consecutive visits, each separated 4 weeks apart. The success rate of achieving total eradication is determined in each group and compared between the two groups using Fisher's exact ($X^2$) test, where $p<0.05$ is considered statistically significant.

Aim 1: To determine whether the weekly office lid massage with a tea tree oil ointment by the patient is equivalent to the weekly office lid scrub with 50% tea tree oil solution by the doctor in reducing ocular *Demodex* counts but free of ocular irritation if both regimens are followed by the same daily home lid scrub with tea tree shampoo.

A pilot study in a total of 15 patients is performed using three different concentrations of tea tree oil ointments (n=5 in each group for these three different concentrations). Each patient performs office lid massage under the doctor's instruction/supervision using one of these three tea tree oil ointments in the doctor's office. The irritating symptoms, if noted after massage, will be graded by OSDI scores and compared to those recorded before the massage. The highest concentration of tea tree oil ointment that does not cause irritation in all 5 patients is used for the remaining study.

A total of 30 patients, meeting inclusion and exclusion criteria, are randomized to either the Control Group (n=15) to receive weekly office lid scrub with 50% tea tree oil solution performed by the doctor or the Study Group (n=15) to receive weekly office lid massage with a tea tree oil ointment performed by the patient. Afterwards, all patients in either group perform home lid scrub with tea tree shampoo, twice a day. All patients undergo follow up visits and examinations as described above, and the outcome measures are determined and compared at the end of the study within the group and between groups.

Aim 2: To determine whether daily lid massage by the patient at home is more effective than weekly lid massage by the patient in the office with a tea tree oil ointment, which is followed by daily home lid scrub with tea tree shampoo, in reducing ocular *Demodex* counts.

A total of 30 patients meeting inclusion and exclusion criteria are randomized into either the Study Group or the Control Group (n=15 each). The Study Group receives daily lid massage with tea tree oil ointment, twice a day, at home, with each followed by washing the residual ointment off from the surrounding lid skin by a face cloth (to reduce the prolonged effect caused by residual tea tree oil ointment). The Control Group is either the same as the Control Group of Aim 1 using the reported Lid Scrub Regimen or the Study Group of Aim 1. All patients undergo follow up visits and examinations as described above, and the outcome measures are determined and compared at the end of the study within the group and between groups.

Aim 3: To determine whether daily lid massage with a tea tree oil ointment by the patient at home without washing it off between massages is more effective in eradicating ocular *Demodex* infestation by preventing mite re-infestation.

A total of 40 patients meeting inclusion and exclusion criteria are randomized into either the Study Group or the Control Group (n=20 each). Both Groups will receive the same daily lid massage with tea tree oil ointment, twice a day, as described in Aim 2. The remaining ointment will be washed away by tap water followed by wiping with a face towel in the Control group, but will be left on the lid skin around the eye in the Study Group. All patients undergo follow up visits and examinations as described above, and the outcome measures are determined and compared at the end of the study within the group and between groups.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A cleaning device comprising a solution consisting essentially or:
    a. about 1% up to, but not including, 20% w/w of terpinen-4-ol as an agent; and
    b. at least one ophthalmically acceptable excipient,
    wherein the solution does not include tea tree oil.

2. The cleaning device of claim 1, wherein the solution further comprises one or more pharmaceutically acceptable ointment bases.

3. The cleaning device of claim 1, wherein the solution further comprises one or more mucoadhesive polymers.

4. The cleaning device of claim 1, wherein the dispenser is wetted with the solution.

5. The cleaning device of claim 1, wherein the dispenser is a cotton applicator.

6. A method of cleaning the skin of an individual, comprising contacting the skin of the individual with the cleaning device of claim 1.

7. The method of claim 6, wherein contacting the skin of the individual with the cleaning device comprises scrubbing the skin with the cleaning device.

8. The method of claim 6, wherein contacting the skin of the individual with the cleaning device comprises washing the skin with the cleaning device.

9. The method of claim 6, wherein the skin comprises a face, eye, eyelid, eyelid margin, eyelash, eyelash roots or a combination thereof.

10. The method of claim 6, comprising contacting the skin of the individual with the cleaning device for at least 4 weeks.

11. The method of claim 6, comprising contacting the skin of the individual with the cleaning device daily.

12. The method of claim 6, comprising contacting the skin of the individual with the cleaning device twice daily.

13. The method of claim 6, wherein the dispenser is wetted with the solution.

14. The method of claim 6, wherein the dispenser is a cotton applicator.

15. The method of claim 6, wherein said cleaning comprises treating an ocular *Demodex* infestation or *Demodex*-induced blepharitis in the individual.

16. The method of claim 6, wherein the individual is refractory to an anti-inflammatory, conventionally anti-microbial antibiotic, or an anti-allergy therapy for ocular *Demodex* infestation or *Demodex*-induced blepharitis.

* * * * *